United States Patent [19]

Tack et al.

[11] Patent Number: 4,814,175

[45] Date of Patent: Mar. 21, 1989

[54] NIFEDIPINE COMBINATION PREPARATION

[75] Inventors: Johannes-Wilhelm Tack; Manfred Albring; Fred Windt-Hanke, all of Berlin, Fed. Rep. of Germany

[73] Assignee: Schering Aktiengesellschaft, Berlin and Bergkamen, Fed. Rep. of Germany

[21] Appl. No.: 132,094

[22] PCT Filed: Mar. 18, 1987

[86] PCT No.: PCT/DE87/00113

§ 371 Date: Nov. 23, 1987

§ 102(e) Date: Nov. 23, 1987

[87] PCT Pub. No.: WO87/05511

PCT Pub. Date: Sep. 24, 1987

[30] Foreign Application Priority Data

Mar. 21, 1986 [DE] Fed. Rep. of Germany ....... 3610037

[51] Int. Cl.$^4$ .......................... A61K 9/48; A61K 9/54
[52] U.S. Cl. .................... 424/453; 424/451; 424/456; 424/457; 424/458; 424/459
[58] Field of Search ............... 424/453, 456, 452, 458, 424/459, 457, 451

[56] References Cited

U.S. PATENT DOCUMENTS

| | | | |
|---|---|---|---|
| 4,281,654 | 8/1981 | Shell et al. | 424/427 |
| 4,510,150 | 4/1985 | Berthold | 514/338 |
| 4,668,770 | 5/1987 | Boger | 530/330 |
| 4,690,935 | 9/1987 | Taylor et al. | 514/255 |

FOREIGN PATENT DOCUMENTS

| | | |
|---|---|---|
| 0142561 | 5/1985 | European Pat. Off. . |
| 0165450 | 12/1985 | European Pat. Off. . |
| 2084017 | 4/1982 | United Kingdom . |

OTHER PUBLICATIONS

The Merck Index, Tenth Edition "Mepindolol" pp. 835–836, No. 5684 Merck & Co. (1983).

Primary Examiner—Thurman K. Page
Attorney, Agent, or Firm—Millen & White

[57] ABSTRACT

The invention relates to nifedipine combination preparations, containing nifedipine with delayed release of active agent and a β-blocker in each case in granulated form, and their pharmaceutical usage as a therapeutic agent in cardiovascular diseases.

6 Claims, No Drawings

NIFEDIPINE COMBINATION PREPARATION

The invention relates to nifedipine combination preparations, containing nifedipine with timed release of active agent and a β-blocker, respectively in granulated form, and their pharmeceutical usage as therapeutics in cardiovascular diseases.

German Laid-Open Application DOS No. 3,419,130 describes formulations for nifedipine already pertaining to the state of the art wherein the bioavailability of the sparingly soluble nifedipine has been improved. Possibilities for improving bioavailability are furthermore described by S. H. Yalkowskay in "Drugs and the Pharmaceutical Science", 12: 135 (1981) and by J. Polderman in "Formulation and Preparation of Dosage Forms", 215 (1977), Elsevier, and include grinding of active compound particles, alterations of crystalline structure, addition of wetting agents, or formation of coprecipitates, to name just a few.

European Laid-Open Application EP No. 142,561 claims a nifedipine formulation with release being uniform over a relatively long time period, consisting of a rapidly released composition A and a retarded-release composition B. In both compositions, the nifedipine particles are larger than 5 μm. The slow release of active agent is obtained by coating the nifedipine-containing (such as mono-, di- or triglycerides, hydrogenated oils, and ethylcellulose) and of lacquer materials resistant to gastric acid.

DOS No. 3,318,649 cites a two-phase nifedipine preparation wherein the particle size of the nifedipine used is 1–10 μm, and the nifedipine crystals have a specific surface area of 1.0–4.0 m²/g.

The present invention concerns a combination preparation, containing 1 part by weight of nifedipine and 0.05–0.25 part by weight of a β-blocker, and customary auxiliary agents and excipients.

The present invention relates, in particular, to the combination preparation of nifedipine and mepindolol. A preferred combination contains 0.05–0.25 part by weight of mepindolol per 1 part by weight of nifedipine. The particle diameter of the nifedipine employed is 10–50 μm, preferably 15–50 μm. The combinations of this invention are prepared by granulating, in each case separately, mepindolol and nifedipine with conventional auxiliary agents and excipients with the aid of a moist granulation process or dry compacting process; optionally coating the granules with lacquer; and dispensing same into hard gelatin capsules. Suitable auxiliary agents are amylose, modified starch, cellulose, cellulose derivatives, crosslinked polyvinylpyrrolidone (PVPP), sodium alginate and colloidal silicon dioxide, gelatin, glucose syrup, starch mucilage, polyethylene glycol, alginates, magnesium stearate, calcium stearate, stearic acid, paraffin, talc, vegetable or animal fats, oils, and waxes.

Suitable fillers that can be cited are calcium sulfate, calcium carbonate, di- and tribasic calcium phosphates, magnesium carbonate, magnesium hydroxycarbonate, sodium chloride, sodium, potassium and calcium citrates, tartrates and succinates, starch, modified starch, cornstarch, cellulose, cellulose powder, hydroxypropylcellulose, sugars, such as lactose, sucrose or dextrose, and sugar alcohols, such as mannitol or sorbitol.

Further auxiliary agents and excipients used are hydroxypropylmethylcellulose phthalate, cetyl alcohol, ethylcellulose, titanium dioxide, hydrogenated castor oil, polysorbate 80, sodium lauryl sulfate, methacrylic acid copolymer (such as "Eudragit" S 100).

The combined use of nifedipine and mepindolol affords the advantage over conventional preparations that a 24-hour long reduction in blood pressure is achieved even with a reduced dose of nifedipine and mepindolol. The amount of β-blocker used ranges, with 0.05–0.25 part by weight per part by weight of nifedipine, markedly below the amount of 0.5–10 parts by weight of β-blocker per part by weight of nifedipine, disclosed in DOS No. 3,419,130.

EXAMPLES

Example 1

(a) 25 g of mepindolol sulfate is premixed for about 10 minutes with 300 g of calcium citrate and 5 g of magnesium stearate in a "Turbula" mixer. The mixture of active agent is added in a suitable mixer to a mixture of 315 g of lactose, 315 g of cornstarch, and 240 g of microcrystalline cellulose and then granulated with purified water into a plastic mass. The moist granulated material is extruded through a screen with a mesh width of 1.0 mm φ and then rounded into pellets in a "Spheronizer". The moist granules (pellets) are dried, for example in a fluidized bed dryer, until the outlet temperature is 50° C. The pellets can subsequently be coated with a light-impervious lacquer.

(b) 400 g of nifedipine (15–50 μm) is suspended in a solution of 80 g of polysorbate 80, 16 g of sodium lauryl sulfate, 200 g of ethanol absolute, and 300 g of demineralized water. This granulating fluid is used for granulating a premix of 1,070 g of mannitol, 100 g of microcrystalline cellulose, 100 g of hydroxypropylcellulose, and 100 g of lactose to obtain a plastic mass. The moist granulated material is extruded through a screen having a mesh width of 1.0 mm φ and then rounded into pellets with a "Spheronizer". The moist granules (pellets) are dried, for example in a fluidized bed dryer, until the outlet temperature is 50° C. 500 g of the dry pellets is coated in the fluidized bed with a solution of 60 g of hydroxypropylmethylcellulose phthalate, 3.2 g of cetyl alcohol, 600 g of ethanol absolute, and 900 g of dichloromethane.

Pellets with mepindolol sulfate (according to a) and nifedipine (according to b) are dispensed into hard gelatin capsules in correspondence with the desired doses (for example: 2.5 mg of mepindolol sulfate and 20 mg of nifedipine).

Example 2

(a) 25 g of mepindolol sulfate is premixed for about 10 minutes with 60 g of calcium citrate and 2.5 g of magnesium stearate in a "Turbula" mixer. The mixture of active compound is admixed in a suitable mixer to a granulated material of 315 g of lactose, 315 g of cornstarch, 240 g of microcrystalline cellulose, and 240 g of calcium citrate. An amount of 2.5 g of magnesium stearate is added to the compound mixture, and the latter is mixed for 0.5 minute. The press-molding composition is pressed into microtablets of, for example, 3 mm diameter. The microtablets can subsequently be coated in the fluidized bed with a lacquer of hydroxypropylcellulose, ethylcellulose, talc, titanium dioxide, and hydrogenated castor oil.

(b) 400 g of nifedipine (15–50 μm) is suspended in a solution of 80 g of polysorbate 80, 16 g of sodium lauryl sulfate, 200 g of ethanol absolute, and 300 g of demineralalized water. This granulating fluid is used for granulating a premix of 1,070 g of mannitol, 100 g of microcrystalline cellulose, 100 g of hydroxypropylcellulose, and 100 g of lactose into a plastic mass. The moist granulated material is extruded through a screen with 1.0 mm φ mesh width and subsequently rounded into pellets in a "Spheronizer".

The moist granules (pellets) are dried, for example in a fluidized bed dryer, until the outlet temperature is 50° C. 500 g of the dry pellets is coated in the fluidized bed with a solution of 48 g of yydroxypropylmethylcellulose phthalate, 12 g of methacrylic acid copolymer (e.g. "Eudragit" S 100), 3.2 g of cetyl alcohol, 600 g of ethanol absolute, and 900 g of dichloromethane.

Microtablets with mepindolol sulfate (according to a) and pellets with nifedipine (according to b) are dispensed into hard gelatin capsules in correspondence with the desired doses (for example, 2.5 mg of mepindolol sulfate and 20 mg of nifedipine).

Example 3

(a) A premix is prepared from 25 g of mepindolol sulfate with 60 g of calcium citrate and 5.0 g of magnesium stearate for about 10 minutes in a "Turbula" mixer. The mixture of active compound is admixed in a suitable mixer to a granulated composition of 315 g of lactose, 315 g of cornstarch, 240 g of microcrystalline cellulose, and 240 g of calcium citrate.

(b) 440 g of nifedipine (15–50 μm) is suspended in a solution of 17.5 g of sodium lauryl sulfate, 220 g of ethanol absolute, and 380 g of demineralized water. With this granulating fluid, a premix of 1,080 g of mannitol, 100 g of microcrystalline cellulose, 100 g of hydroxypropylcellulose, and 100 g of lactose is granulated into a plastic mass. The moist granulated material is extruded through a screen having a mesh width of 1.0 mm φ and then rounded to pellets in a "Spheronizer". The moist granules (pellets) are dried, for example in a fluidized bed dryer, until the outlet temperature is 50° C. 500 g of the dry pellets is coated in the fluidized bed with a solution of 60 g of hydroxypropylmethylcellulose phthalate, 3.2 g of cetyl alcohol, 600 of ethanol absolute, and 900 g of dichloromethane.

Granulated materials with mepindolol sulfate (according to a) and pellets with nifedipine (according to b) are filled into hard gelatin capsules in correspondence with the desired doses (for example 2.5 mg of mepindolol sulfate and 20 mg of nifedipine).

We claim:

1. A gelatin capsule containing 1 part by weight of granulated nifidepine having a particle diameter of 10–50 μm and 0.01–0.5 parts by weight of granulated mepindolol.

2. The capsule of claim 1 wherein both the granulated nifidepine and granulated mepindolol are coated before dispensing into the capsule.

3. The capsule of claim 1 further comprising auxiliary agents and excipients added before granulation.

4. Combination preparation according to claim 1, characterized in that the nifedipine component of the combination exhibits retarded release of active compound.

5. A process for treating cardiovascular disease which comprises the administration of the capsule of claim 1.

6. Combination preparation according to claim 1, characterized in that the granulated nifedipine and the granulated mepindolol are provided in one two-piece capsule.

* * * * *